(12) United States Patent
Schulze et al.

(10) Patent No.: US 6,173,198 B1
(45) Date of Patent: Jan. 9, 2001

(54) APPARATUS AND METHOD FOR THE ACCURATE PLACEMENT OF BIOMEDICAL SENSORS

(75) Inventors: Arthur E. Schulze, Wharton, TX (US); Tuan Bui, Green Oaks, IL (US); Clint Deckert, Poway, CA (US)

(73) Assignee: Baxter International Inc., Deerfield, IL (US)

( * ) Notice: Under 35 U.S.C. 154(b), the term of this patent shall be extended for 0 days.

(21) Appl. No.: 09/240,523

(22) Filed: Jan. 29, 1999

(51) Int. Cl.[7] .................................................. A61B 5/0402
(52) U.S. Cl. ........................... 600/382; 600/386; 600/393
(58) Field of Search .................................. 600/372, 382, 600/386, 393

(56) References Cited

U.S. PATENT DOCUMENTS

| 4,121,575 | 10/1978 | Mills et al. . |
|---|---|---|
| 4,583,549 | 4/1986 | Manoli . |
| 4,957,109 | 9/1990 | Groeger et al. . |
| 5,042,481 | * 8/1991 | Suzuki et al. .................... 600/393 |
| 5,184,620 | 2/1993 | Cudahy et al. . |
| 5,224,479 | 7/1993 | Sekine . |
| 5,321,618 | 6/1994 | Gessman . |
| 5,445,149 | 8/1995 | Rotolo et al. . |
| 5,678,545 | 10/1997 | Stratbucker . |
| 5,865,741 | * 2/1999 | Kelly et al. .................... 600/386 |

* cited by examiner

*Primary Examiner*—Lee Cohen
(74) *Attorney, Agent, or Firm*—Matthew J. Gryzlo; Wallenstein & Wagner

(57) ABSTRACT

A positioning device for the accurate placement of biomedical sensors. The positioning device has a template frame and one or more template arms. The template frame is able to be referenced to at least one anatomical site upon the human body, such as the sternal notch or the navel. Template arms extend from the template frame to the electrode positioning site. The length and angle of the template arms corresponds to the distance from the template frame to the electrode positioning site. The template arms reference the electrode positioning sites with respect to the template frame. The template frame references the template arms with respect to anatomical sites upon the human body.

33 Claims, 4 Drawing Sheets

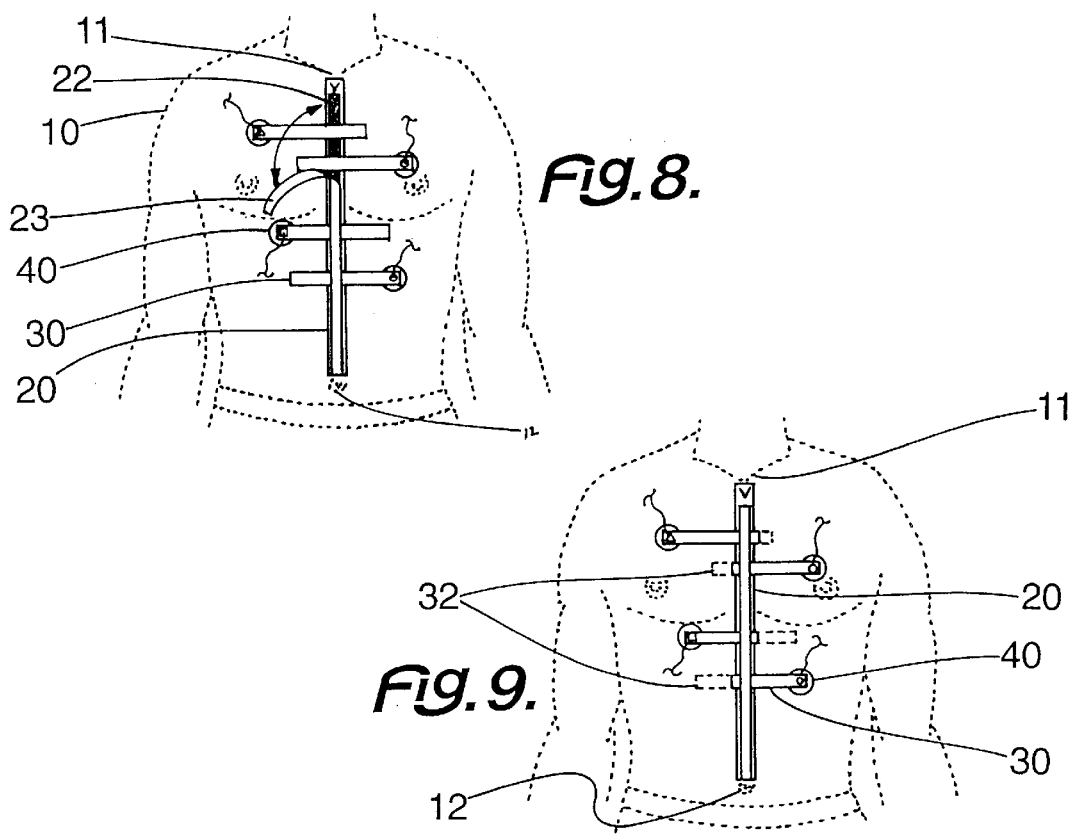
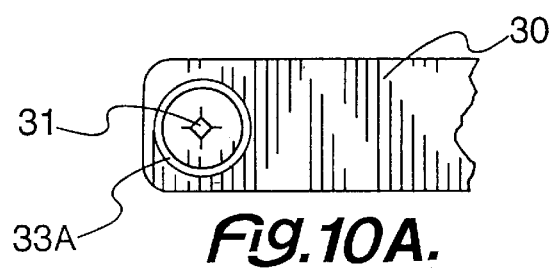
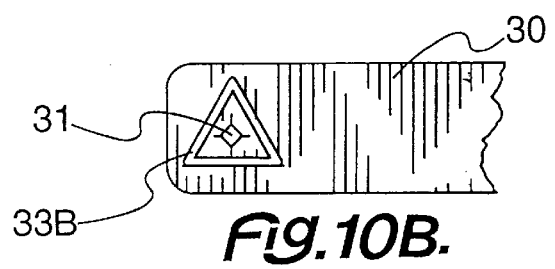

APPARATUS AND METHOD FOR THE ACCURATE PLACEMENT OF BIOMEDICAL SENSORS

FIELD OF THE INVENTION

This invention relates in general to biomedical monitoring, and more particularly to a method and apparatus for use in accurately placing biomedical sensor electrodes upon a patient's body for electrocardiographic recordings and the like.

BACKGROUND OF THE INVENTION

Analytical diagnostics which are made by utilization of electrocardiograms (ECGs) have been generally used for diagnosis and monitoring of various forms of cardiopathologies, such as for patients with implanted pacemakers. As one of existing electrocardiographs, there has been widely used the so-called trans-telephonic monitor for use in trans-telephonic medicine, i.e. the reading of data to be sent, e.g. over the telephone line, to a special facility where the diagnosis is performed remotely at a central facility, such as described in U.S. Pat. No. 5,321,618 to Gessman for "Apparatus and Method for Remotely Monitoring Implanted Cardioverter Defibrillators", issued Jun. 14, 1994. This is especially useful for the long-term monitoring of patients, with e.g. heart trouble, because it reduces the need for the patient to go to a clinic or hospital. Trans-telephonic medicine and home monitoring is also useful for the control of patients, with e.g. heart trouble, residing in localities without adequate medical facilities.

In the art of electrocardiographic recordings, one of the essential conditions for successful recording is the correct biomedical sensor electrode positioning on the body. Incorrect biomedical sensor electrode positioning can make diagnosis and treatment difficult or erroneous. Typically a specially trained health care professional will demonstrate to a patient the correct placement of the biomedical sensor electrodes. The patient is then expected to be able to correctly position the biomedical sensor electrodes. This can be a problem because patients must remember the correct placement sites, often after a significant amount of time has passed since the initial demonstration.

Each human body is unique, and the placement sites for biomedical sensors vary among individuals. Incorrect electrocardiographic recordings can result if the template is not adaptable to each individual patient. Use of an adjustable vest with built-in biomedical sensor electrodes to provide for correct positioning of the biomedical sensor electrodes has been known in the art. Examples of vests with built-in biomedical sensor electrodes include U.S. Pat. No. 5,224,479 to Sekine for "ECG Diagnostic Pad", issued Jul. 6, 1993, and U.S. Pat. No. 5,445,149 to Rotolo et al. for "Electrocardiography Electrode Positioning Device", issued Aug. 29, 1995. The vests known in the art also can be uncomfortable. The vests are more intrusive than just biomedical sensor electrodes because they must surround the entire torso to achieve accurate biomedical sensor electrode placement. The vests must also fit the torso tightly to achieve consistent placement of biomedical sensor electrodes.

It would be desirable to provide an inexpensive technique for repetitive and accurate placement of biomedical sensor electrodes for medical diagnosis and at-home patient monitoring. For the foregoing reasons, there is a need for an inexpensive, adaptable technique that can be used as a reference for the accurate placement of sensors upon an individual human body, which also facilitate subsequent placement of such biomedical sensor electrodes.

SUMMARY OF THE INVENTION

The present invention is directed to an apparatus that satisfies the need for assistance in accurate sensor placement by the at-home patient, to this end a template may be used as a reference for the accurate placement of sensors upon the human body.

The apparatus may include an adaptable template which may be used for accurate placement of biomedical sensor electrodes, the template has a template frame that may be positioned, e.g., with respect to at least one anatomical site on the human body, such as the sternal notch. At least one template arm may be connectable to the template frame. The template arms extend from the placement sites for the biomedical sensor electrodes to the template frame. The lengths of the template arms and the template frame then can be adjusted to provide accurate referencing for the correct placement of biomedical sensor electrodes upon an individual patient.

The apparatus and method described in this manner may thus adapt to each unique human individuals' body. The distance between the desired placement site of the sensors and the template frame can be adjusted by trimming the template arm to the necessary length. By defining the distance between the placement site of the sensors and the template frame, and then referencing the template frame to the unique anatomy of an individual patient, the accurate placement of sensors is achieved.

Unlike vests used for positioning biomedical sensor electrodes, the adjustable template is inexpensive and has the advantage of using standard sensors. The use of standard electrodes reduces the cost of the apparatus. The use of a template is further distinguished from vests because the vests must be worn. The template is not worn and therefore reduces patient discomfort.

Briefly summarized, the present invention relates to a positioning device for the accurate placement of biomedical sensor electrodes. The positioning device in a preferred embodiment has a template frame and one or more template arms. The template frame is able to be referenced to at least one anatomical site upon the human body, such as the sternal notch or the navel. Template arms extend from the template frame to the biomedical sensor electrode positioning site. The length of the template arms corresponds to the distance from the template frame to the biomedical sensor electrode positioning site. The template arms reference the biomedical sensor electrode positioning sites with respect to the template frame. The template frame references the template arms with respect to anatomical sites upon the human body. In this manner, a positioning device is provided for the correct placement of biomedical sensor electrodes upon an individual human body.

These and other features, aspects, and advantages of the present invention will become better understood with regard to the following description, appended claims, and accompanying drawings.

BRIEF DESCRIPTION OF THE DRAWINGS

FIG. 8 is a frontal view of a template frame superimposed upon a human body with template arms attached to the adhesive strip under the adhesive strip protector with the biomedical sensor electrodes inserted in the template arm holes;

FIG. 9 is a frontal view of a template with the template arm overlap removed.

DETAILED DESCRIPTION OF THE PREFERRED EMBODIMENTS

Figure 1:
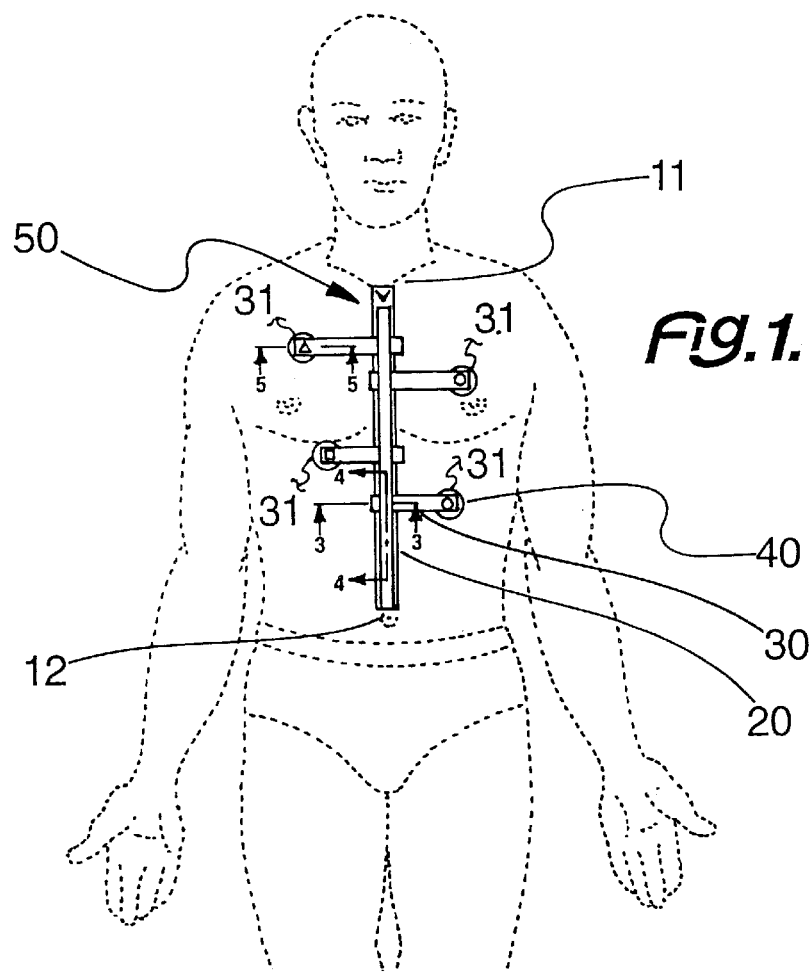
FIG. 1 is a frontal view of a template superimposed upon a human body.

With reference to the figures and particularly FIG. 1, a positioning device 50 is provided in accordance with the present invention. The positioning device 50 includes a template frame 20 and template arms 30 with template armhole 31 provided for insertion of biomedical sensor electrodes 40 including electrocardiographic electrodes.

Figure 2:
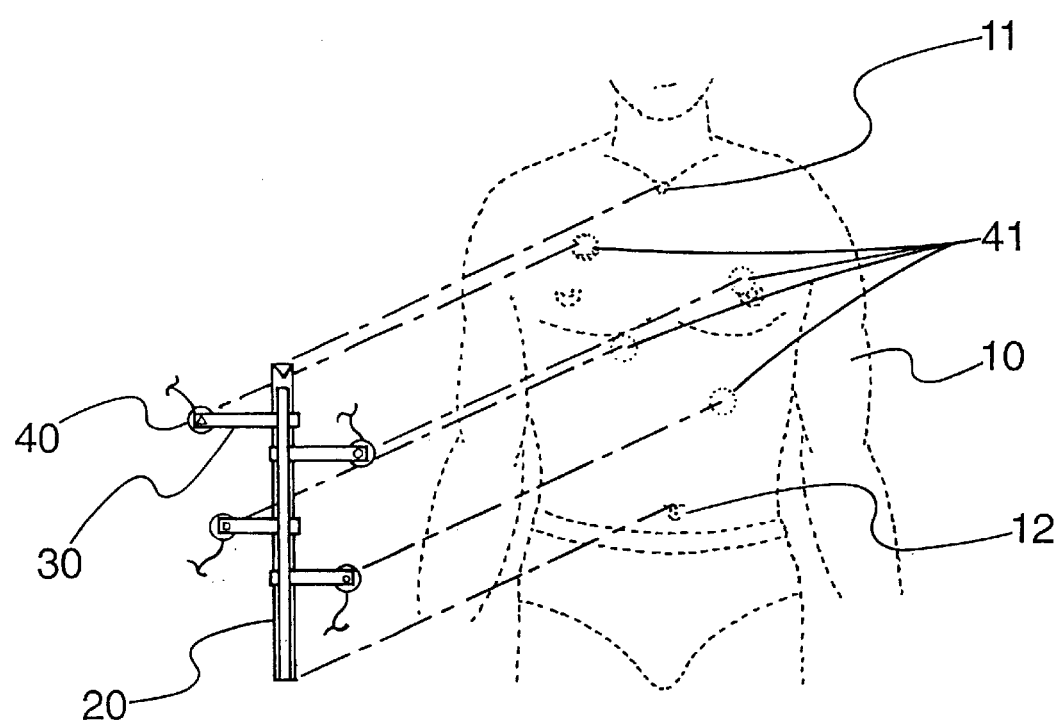
FIG. 2 is a frontal view of a template removed a distance from a human body.

For example, the template frame 20 is positioned relative to the human body 10 by reference to the sternal notch 11 and the navel 12 as shown in FIG. 2. Reference to other anatomical features of the human body 10 are contemplated, depending upon the size of the device and the characteristics of the individual.

Figure 3:
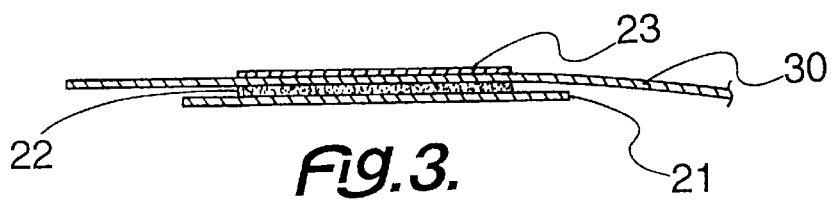
FIG. 3 is a view taken along line 3—3 of FIG. 1.
Figure 4:
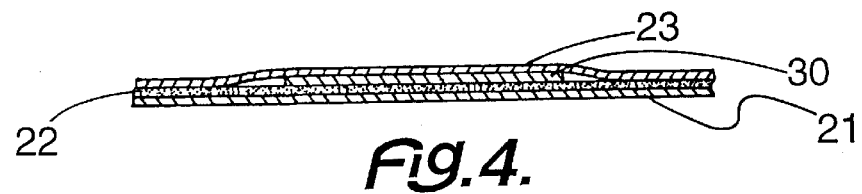
FIG. 4 is a view taken along line 4—4 of FIG. 1.

The template arms 30 are fixed relative to the template frame 21 using an adhesive strip 22 covered by an adhesive strip protector as shown in FIGS. 3 and 4. The use of an adhesive strip 22 has the advantage of securing the template arms 30 to the template frame 21 so that during normal use by an individual the template arms 30 are fixed a correct distance and angle relative to the template frame 21 and resist movement. Other means of fixing the template arms 30 relative to the template frame 21 can include a velcro-type strip in the place of the adhesive strip 22 or staples. The adhesive strip protector 23 covers the adhesive strip 22 and portions thereon where there are no template arms 30 preventing the adhesive strip 22 from attaching to anything other than the template arms 30.

Figure 5:
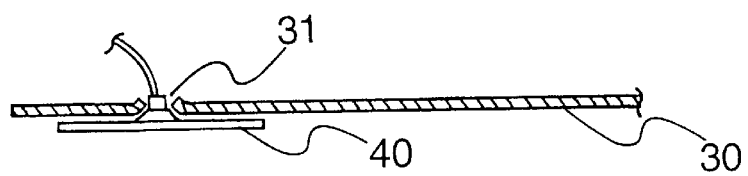
FIG. 5 is a view taken along line 5—5 of FIG. 1.

The template arms 30 have template arm holes 31 disposed on an end of the template arms 30 opposite the template frame 21 for insertion of biomedical sensor electrodes 40 as shown in FIG. 5. The template arms do not have to be placed perpendicular to the template frame 20. When the biomedical sensor electrodes 40 are inserted into the template arm holes 31 of the template arms 30, the device can easily and quickly be used by an individual for aligning the biomedical sensor electrodes 40 with the biomedical sensor electrode positioning sites 41 upon the human body 10.

Figure 6:
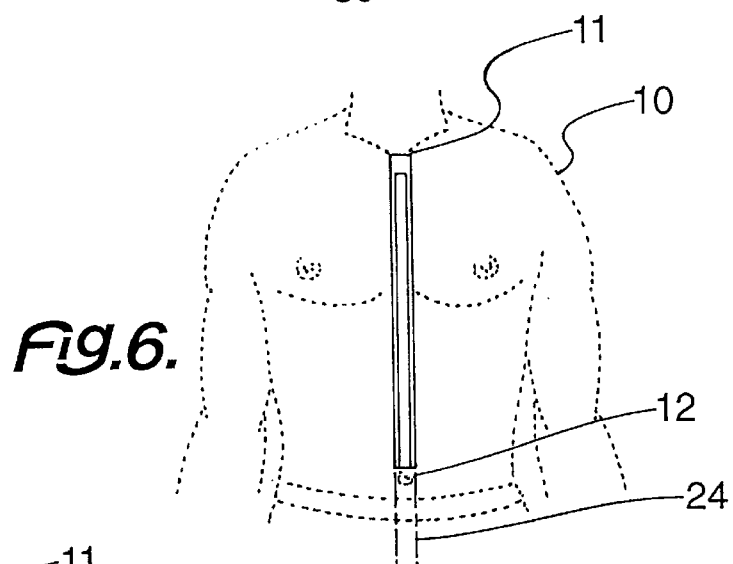
FIG. 6 is a frontal view of a template frame superimposed upon a human body with the template frame overlap removed.
Figure 7:
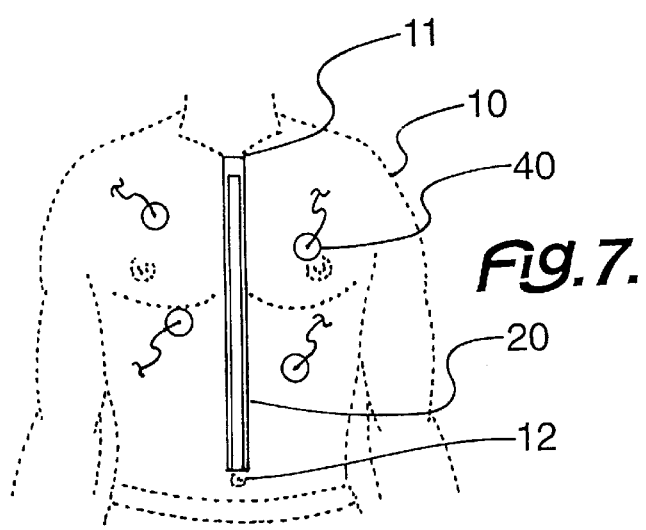
FIG. 7 is a frontal view of a template frame superimposed upon a human body showing the placement of biomedical sensor electrodes upon the human body.

The positioning device 50 can be adjusted to reference biomedical sensor electrode positioning sites 41 of the biomedical sensor electrodes 40 to fit an individual human body 10. As shown in FIG. 6, the template frame 20 can be superimposed upon the human body 10 by positioning relative to the sternal notch 11 and the navel 12. A template frame overlap 24, the portion of the template frame 20 extending past the navel 12, can be removed so that the template frame 20 extends from the sternal notch 11 to the navel 12 upon the human body 10.

The invention can be used for locating the placement sites 41 of biomedical sensor electrodes 40 upon a human body 10. The template frame 20 has at least one reference location for positioning relative to one or more anatomical sites upon the human body 10. One or more template arms 30 are provided for locating the placement sites 41 of biomedical sensor electrodes 40 upon the human body 10 with respect to the template frame 20. The template arm 30 can be connected to the template frame 20 for defining the distance from an end of the template arm 30 disposed opposite of the template frame 20 to the template frame 20.

Figure 10C:
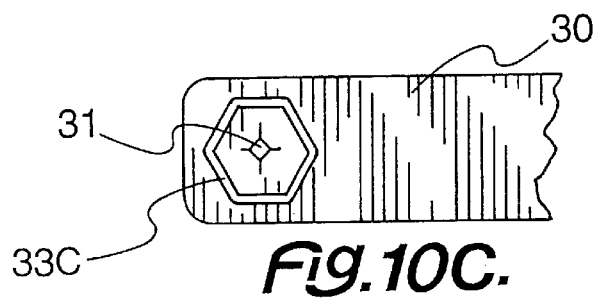
FIGS. 10(a–d) are views of the template arms with indicia shown.
Figure 10D:
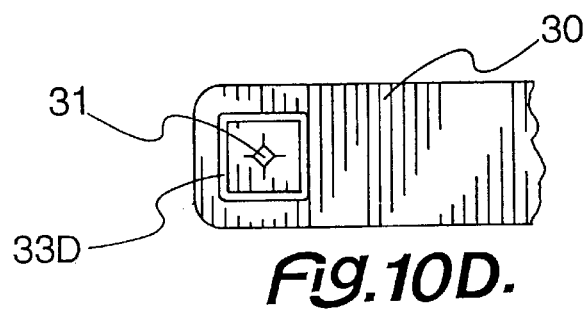

The template arms 30 are provided with template arm indicium 33 to distinguish among different template arms 30. The template arm indicium 33 (A–D) can consist of geometric shapes, such as a circle, triangle, hexagon, and square, as depicted in FIGS. 10 (A–D). The template arm indicium 33 (A–D) can also consist of descriptive words and phrases, alone or in conjunction with geometric shapes. Examples of some descriptive words or phrases include "LL ELECTRODE", "GND ELECTRODE", and "RA ELECTRODE." The template plate arm indicium 33 (A–D) can further consist of identifying colors that can be used to distinguish between the different template arms 30.

The template arms 30 and the template frame 20 can be made from a flexible material to increase the safety of use of the invention and prevent the invention from sustaining damage. In a particular embodiment of the invention, the template frame 20 and the template arms 30 can be made of cardboard that is laminated for durability.

In another embodiment of the apparatus which comports with the illustrated shown in FIG. 9, the invention includes a template frame 20, and four template arms 30. The first, second, and third template arms 30 have a biomedical sensor electrode 40 located in the template arm hole 31 thereof, respectively. The biomedical sensor electrode 40 in the first template arm 30 is located at a first position on the human body, and is also known in the art as a lower limb lead electrode equivalent. The biomedical sensor electrode 40 in the sensor template arm 30 is located at a second position on the human body, and is also known in the art as an upper limb lead electrode equivalent. The biomedical sensor electrode 40 in the third template arm 30 is located at a third position on the human body, and is also known in the art as a precordial lead electrode equivalent. The fourth template arm 30 is provided for locating a placement site of a temperature sensor. The template arms 30 are connected to the template frame 20 for defining the distance from an end of the template arm 30 to the template frame.

A representative method for use of the invention begins with first placing the upper edge of the template frame 20 at the sternal notch 11 upon a human body 10. The template frame 20 should extend in a longitudinal direction parallel to the sternum. The template frame 20 is of a length such that the template frame 20 extends past the navel 12 upon the human body 10. The portion of the template frame 20 that extends past the navel 12 upon the human body 10 is the template frame overlap 24. The template frame overlap 24 can be removed, e.g. with scissors, in an embodiment of the invention wherein the template frame 20 is made of laminated cardboard. The template frame 20 can thus be adjusted to a length corresponding to the distance between the sternal notch 11 and the navel 12 of an individual human body 10.

The second step of a method for use of the invention involves placing the biomedical sensor electrodes 40 at the their desired locations upon the human body 10. The template arm holes 31 of the template arms 30 can be placed such that the biomedical sensor electrodes 40 extend into the template arm holes 31. The ends of the template arms 30 opposite the ends of the template arms 30 with the template arm holes 31 can then be extended past the template frame 20. The adhesive strip protector 23 can be peeled away from the adhesive strip 22 of the template frame 20 to allow the template arms 30 to secure to the adhesive strip 22. The adhesive strip protector 23 can then be placed back upon the portions of the adhesive strip 22 without attached template arms 30.

The invention, illustrated for example with a template frame 20, attached template arms 30, and biomedical sensor electrodes 40 located in template arm holes 31 of the template arms 30, can then easily be used repetitively by an individual for the correct positioning of biomedical sensor electrodes 40 upon the individual human body 10.

Figure 11:
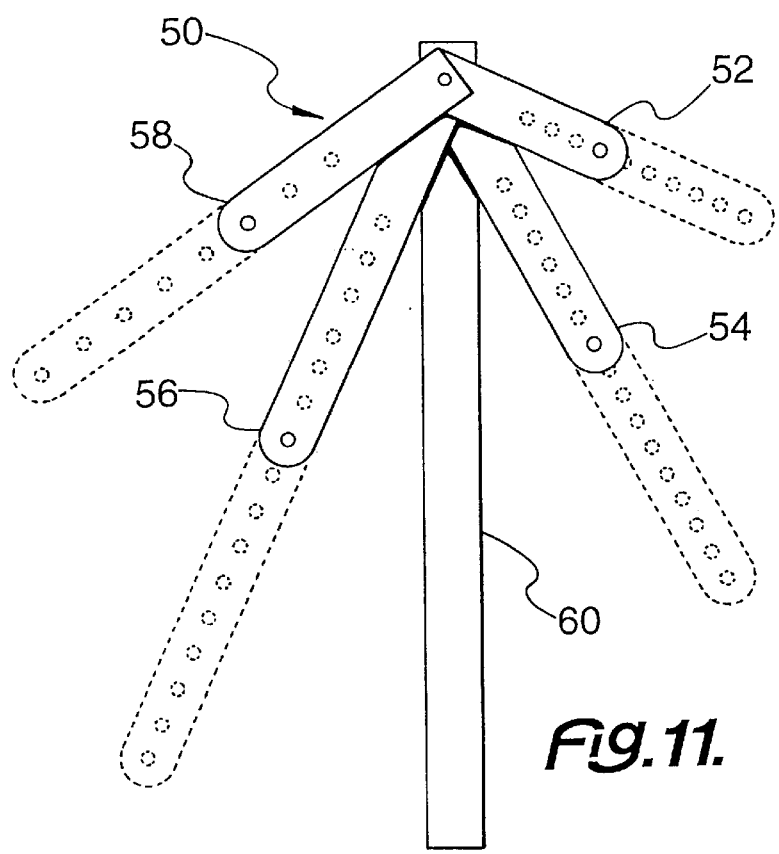
FIG. 11 is a fan type alternate embodiment in accordance with the invention.

An alternate embodiment of the above-described invention may include a "fan" type arrangement as shown in connection with FIG. 11. The alternate embodiment 50 includes fan type arms 52, 54, 56, and 58 mounted on a template frame 60. The fan type arrangement with arms extending from the top provides an indication of the positioning of the biomedical sensor electrodes from the template body 60. The arms 52, 54, 56, and 58 may include a set of pre-drilled holes in each of the arms which may be used for position determination of the biomedical sensor electrodes. Puncture holes may also be used for defining this position as well. It is contemplated in accordance with the described embodiment that lengths of the arms may be cut away, as indicated by the dashed lines, such that the physician cuts away arms to the length desired for the positioning of the biomedical sensor electrodes relative to the template frame.

It will be appreciated that although various aspects of the invention have been described with respect to specific embodiments, alternatives and modifications will be apparent from the present disclosure, which are within the spirit and scope of the present invention as set forth in the following claims.

What is claimed is:

1. An apparatus for locating the placement sites of biomedical sensors upon a human body, comprising:
    a template frame comprising one or more reference locations for positioning of said template frame relative to one or more anatomical sites on said human body;
    one or more template arms for locating said placement sites of biomedical sensors upon said human body with respect to said template frame; and
    said one or more template arms being connectable to said template frame at different vertical locations thereon for defining the distance from an end of said one or more template arms to said template frame and an angle of said one or more template arms to the template frame.

2. An apparatus as recited in claim 1 comprising a plurality of template arms, wherein each of said plurality of template arms comprises indicia to distinguish among said template arms.

3. An apparatus as recited in claim 2 wherein said indicia comprise unique colors on each of said template arms to distinguish among said template arms.

4. An apparatus as recited in claim 2 wherein said indicia comprise unique geometrical shapes on each of said template arms to distinguish among said template arms.

5. An apparatus as recited in claim 2 wherein said indicia comprise written designations on each of said template arms.

6. An apparatus as recited in claim 1 wherein said template arm defines a template opening on the template arm positionable at said placement site, said template opening allowing for insertion of said sensor.

7. An apparatus as recited in claim 1 wherein the reference location of the template frame on said human body are positionable relative to the human navel and the human sternal notch.

8. An apparatus as recited in claim 1 wherein the reference location of the template frame on said human body is positionable relative to the chosen one or more anatomical sites.

9. An apparatus as recited in claim 1 comprising an adhesive bond between said template arm and said template frame for connecting said template arm to said template frame for defining the distance and angle from the end of said template arm to said template frame.

10. An apparatus as recited in claim 1 wherein said template frame and said template arm comprise a flexible material.

11. An apparatus as recited in claim 10 wherein said flexible material of said template frame and said template arm comprises laminated cardboard.

12. An apparatus as recited in claim 1 wherein said template frame and one or more of said template arms are combined into a single package for distribution to patients.

13. A method of locating the placement sites of biomedical sensors upon a human body, comprising:
    placing the upper edge of a template frame near the sternal notch;
    adjusting the length of the template frame so that the bottom edge is near the level of the navel;
    placing biomedical sensors near the desired location of an individual patient;
    placing one end of a template arm in proximity to said biomedical sensor; and
    connecting one end of said template arm on said template frame so that the distance and the angle between said biomedical sensor is fixed relative to said template frame.

14. A method as recited in claim 13 comprising providing said template arm with identifying indicia to distinguish among a plurality of different template arms.

15. A method as recited in claim 13 wherein said placement sites of biomedical sensors can be repetitively located upon said human body by placing the biomedical sensors at the desired location as indicated with the distance between one end of said template arm fixed relative to said template frame.

16. A method as recited in claim 13 wherein adjusting the length of the template frame comprises cutting off a lower portion of said template frame at the level of the navel.

17. A method as recited in claim 13 wherein said template arm comprises a template opening positioned at said placement site allowing for insertion of said sensor.

18. A method as recited in claim 13 wherein a reference location of said template frame on said human body is positionable relative to the human navel and the human sternal notch.

19. A method as recited in claim 13 comprising providing an adhesive bond between said template arm and said template frame for defining the distance from the end of said template arm to said template frame.

20. A method as recited in claim 13 comprising placing biomedical sensors at three desired locations on the patient's torso.

21. A method as recited in claim 13 comprising removing said template frame and one or more of said template arms from a single package.

22. An apparatus for locating the placement sites of electrocardiographic electrodes upon a human body, which comprises:
- a template frame comprising a reference location for positioning of said template frame relative to the human sternal notch;
- a first template arm for locating a placement site of a first electrode on a first position on the human body as a lower limb lead electrode equivalent;
- a second template arm for locating a placement site of a second electrode on a second position on the human body as an upper limb lead electrode equivalent;
- a third template arm for locating a placement site of a third electrode on a third position on the human body as a precordial lead electrode; and
- said template arms being connected to said template frame for defining the distance from an end of said template arm to said template frame.

23. An apparatus as recited in claim 22 wherein said template arms comprise identifying features to distinguish between different template arms.

24. An apparatus as recited in claim 23 wherein said identifying features comprise the written descriptions "LL ELECTRODE", "GND ELECTRODE", and "RA ELECTRODE".

25. An apparatus as recited in claim 22 further comprising a fourth template arm for locating a placement site of a temperature sensor.

26. An apparatus for locating the placement sites of biomedical sensor electrodes upon a human body, comprising:
- means for placing the upper edge of a template frame at the sternal notch;
- means for adjusting the length of the template frame so that the bottom edge is at the level of the navel;
- means for placing biomedical sensor electrodes at the desired location of an individual patient;
- means for placing one end of a template arm on said biomedical sensor electrode; and
- means for connecting one end of said template arm on said template frame so that the distance and the angle between said biomedical sensor electrode is fixed relative to said template frame.

27. An apparatus as recited in claim 26 wherein said connecting means comprises an adhesive bond between said template frame and said template arms.

28. An apparatus for locating the placement sites of biomedical sensors upon a human body, comprising:
- a template frame comprising one or more reference locations for positioning of said template frame relative to one or more anatomical sites on said human body;
- a plurality of template arms for locating said placement sites of biomedical sensors upon said human body with respect to said template frame; and
- said plurality of template arms being connectable to said template frame at substantially the same location on the template frame for defining a distance from an end of said plurality of template arms to said template frame and an angle of said plurality of template arms to the template frame.

29. An apparatus as recited in claim 28 wherein each of said plurality of template arms comprises indicia to distinguish among said template arms.

30. An apparatus as recited in claim 28 wherein said indicia is selected from the group consisting of: unique colors, unique geometrical shapes, and written designations.

31. An apparatus as recited in claim 28 wherein said template arm defines a template opening on the template arm positionable at said placement site, said template opening allowing for insertion of said sensor.

32. An apparatus as recited in claim 28 wherein the reference locations of the template frame on said human body are positionable relative to the human navel and the human sternal notch.

33. An apparatus as recited in claim 28 wherein the reference locations of the template frame on said human body are positionable relative to the chosen one or more anatomical sites.

* * * * *